United States Patent
Saito

(10) Patent No.: US 9,285,274 B2
(45) Date of Patent: Mar. 15, 2016

(54) INFRARED DETECTING ELEMENT AND ELECTRONIC DEVICE

(75) Inventor: Hidetaka Saito, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 901 days.

(21) Appl. No.: 13/546,318

(22) Filed: Jul. 11, 2012

(65) Prior Publication Data

US 2013/0032717 A1 Feb. 7, 2013

(30) Foreign Application Priority Data

Aug. 4, 2011 (JP) ................................ 2011-170778

(51) Int. Cl.
*G01J 5/34* (2006.01)
*G01J 5/20* (2006.01)
*H01L 27/14* (2006.01)
*G01T 1/24* (2006.01)
(Continued)

(52) U.S. Cl.
CPC ............. *G01J 5/0225* (2013.01); *G01J 5/0205* (2013.01); *G01J 5/34* (2013.01); *H01L 31/0203* (2013.01); *G01J 5/0003* (2013.01); *G01J 5/0022* (2013.01); *G01J 5/0025* (2013.01); *G01J 5/023* (2013.01); *G01J 5/024* (2013.01); *G01J 5/10* (2013.01); *G01J 2005/0077* (2013.01); *G01J 2005/106* (2013.01); *G01J 2005/202* (2013.01); *G01J 2005/345* (2013.01); *G01N 21/17* (2013.01); *G01N 21/84* (2013.01); *G01N 2021/0106* (2013.01); *G01N 2201/02* (2013.01); *G01N 2201/0216* (2013.01); *G08B 13/191* (2013.01); *H01L 23/481* (2013.01); *H01L 23/49811* (2013.01); *H01L 23/49827* (2013.01); *H01L 23/52* (2013.01); *H01L 27/14* (2013.01); *H01L 31/02* (2013.01); *H01L 31/024* (2013.01); *H01L 2224/48091* (2013.01); *H01L 2924/3025* (2013.01); *Y10S 250/01* (2013.01)

(58) Field of Classification Search
CPC ............... G01J 5/34; G01J 5/10; H01L 27/14
USPC .............. 250/338.3, 338.4, 370.14, 371, 395; 257/431
See application file for complete search history.

(56) References Cited

U.S. PATENT DOCUMENTS

RE36,615 E *  3/2000  Wood .............................. 338/18
2004/0187904 A1  9/2004  Krellner et al.
(Continued)

FOREIGN PATENT DOCUMENTS

JP    05-240702 A    9/1993
JP    06-022944 U    3/1994
(Continued)

*Primary Examiner* — David Porta
*Assistant Examiner* — Carolyn Igyarto
(74) *Attorney, Agent, or Firm* — Global IP Counselors, LLP

(57) ABSTRACT

The infrared detecting element has a first base plate that has a first front surface, a first back surface, a first recessed portion, and an infrared detecting section for detecting infrared rays provided in an area of the first front surface that opposes the first recessed portion; a second base plate that has a second front surface, a second back surface on the opposite side of the second front surface, and a second recessed portion provided in an area of the second back surface that faces the first recessed portion; and an adhesion film that bonds the first back surface and the second back surface, wherein a second outer peripheral portion where the second recessed portion intersects with the second back surface surrounds a first outer peripheral portion where the first recessed portion intersects with the first back surface.

7 Claims, 10 Drawing Sheets

(51) Int. Cl.
  *G01J 5/02*        (2006.01)
  *H01L 31/0203*     (2014.01)
  *G01N 21/01*           (2006.01)
  *G01J 5/00*            (2006.01)
  *G01J 5/10*            (2006.01)
  *G01N 21/84*           (2006.01)
  *G08B 13/191*          (2006.01)
  *G01N 21/17*           (2006.01)
  *H01L 31/02*           (2006.01)
  *H01L 31/024*          (2014.01)
  *H01L 23/48*           (2006.01)
  *H01L 23/498*          (2006.01)
  *H01L 23/52*           (2006.01)

(56) References Cited

U.S. PATENT DOCUMENTS

2006/0186339 A1   8/2006   Sasaki et al.
2011/0082372 A1   4/2011   Tateyama

FOREIGN PATENT DOCUMENTS

| JP | 06-077504 A   | 3/1994  |
| JP | 08-122160 A   | 5/1996  |
| JP | 2004-361386 A | 12/2004 |
| JP | 2006-226890 A | 8/2006  |
| JP | 2010-017530 A | 1/2010  |
| JP | 2010-050406 A | 3/2010  |

* cited by examiner

INFRARED DETECTING ELEMENT AND ELECTRONIC DEVICE

CROSS-REFERENCE TO RELATED APPLICATIONS

This application claims priority to Japanese Patent Application No. 2011-170778 filed on Aug. 4, 2011. The entire disclosure of Japanese Patent Application No. 2011-170778 is hereby incorporated herein by reference.

BACKGROUND

1. Technical Field

The present invention relates to an infrared detecting element, and particularly relates to an element that detects an irradiation amount of infrared rays.

2. Background Technology

Patent Document 1 has disclosed a bolometer-type infrared detecting element in which a detecting section is provided on a supporting base plate and the supporting base plate has a hollow structure. According to this document, an absorbing section is provided on a bolometer that serves as the detecting section. Infrared rays are converted into heat in the absorbing section, and the detecting section is heated with this heat. It serves as the infrared detecting element by reading change in resistance temperature of the detecting section.

Patent Document 2 has disclosed a method for mounting a sensor chip having a hollow structure on a base plate by die bonding. According to this document, a ventilation means is provided in a base board to which a sensor chip is attached. A space in the hollow structure is connected to outer air by the ventilation means. Consequently, change in pressure is made small at the time of heating and at the time of cooling.

Patent Document 3 has disclosed a method for improving the sensitivity of a sensor chip of a thermocouple having a hollow structure. According to this document, a hollow space is provided in a base portion header on which a sensor chip is mounted so as to increase the space of the hollow structure. Consequently, heat release from the sensor chip is controlled. Hereinafter, a sensor chip is referred to as an infrared detecting element.

Japanese Laid-open Patent Publication No. 2006-226890 (Patent Document 1), Japanese Laid-open Patent Publication No. H06-77504 (Patent Document 2) and Japanese Laid-open Patent Publication No. 2004-361386 (Patent Document 3) are examples of the related art.

SUMMARY

Problem to be Solved by the Invention

In order to fix an infrared detecting element having a hollow structure to a base plate, an adhesive is applied to the infrared detecting element or the base plate so as to attach them. In this instance, if an adhesion film formed of a solidified adhesive is located in a space of the hollow structure, the space is reduced and thus the sensor is not insulated. Accordingly, it has been desired that an infrared detecting element has a structure in which an adhesion film is not easily formed in the space of the hollow structure even when the infrared detecting element is attached to a base plate with an adhesive.

The invention has been made to address at least part of the above-described circumstances, and the invention can be achieved as embodiments or application examples described below.

Means for Solving Problem

Application Example 1

An infrared detecting element of this application example has a first base plate that has a first surface, a second surface on the opposite side of the first surface, a first recessed portion provided in the second surface, and an infrared detecting section for detecting infrared rays provided in an area of the first surface that opposes the first recessed portion; a second base plate that has a third surface, a fourth surface on the opposite side of the third surface, and a second recessed portion provided in an area of the fourth surface that faces the first recessed portion; and an adhesion film that bonds the second surface and the fourth surface, in which a second outer peripheral portion where the second recessed portion intersects with the fourth surface surrounds a first outer peripheral portion where the first recessed portion intersects with the second surface.

According to this application example, the first base plate and the second base plate of the infrared detecting element are bonded with an adhesion film. The first base plate has the first recessed portion in the second surface. The second base plate has the second recessed portion in an area facing the first recessed portion. Consequently, the area sandwiched by the first recessed portion and the second recessed portion becomes a hollow space. The infrared detecting element has the infrared detecting section in an area of the first surface that opposes the first recessed portion.

The infrared detecting section detects an irradiation amount of infrared rays by detecting a temperature rise due to heat by infrared irradiation. Accordingly, the speed of releasing heat from the infrared detecting section needs to be a predetermined speed. The area of the first base plate that opposes the infrared detecting section is a hollow space. Heat transmission is slower in the hollow space than in the first base plate, and thus the speed of releasing heat from the infrared detecting section can be reduced.

The adhesion film is a film formed of a solidified adhesive. When an adhesive flows into the first recessed portion in the process of solidification of the adhesive, the adhesion film is located inside the first recessed portion. In this instance, the hollow space becomes small, and thus heat will be easily released from the infrared detecting section heated by infrared rays. Consequently, the sensitivity of the infrared detecting section will be deteriorated. In the present embodiment, the second recessed portion is provided in an area that faces the first recessed portion. Accordingly, when an adhesive proceeds to the first recessed portion, the adhesive also proceeds to the second recessed portion. Further, since the second outer peripheral portion that is the outer periphery of the second recessed portion surrounds the first outer peripheral portion that is the outer periphery of the first recessed portion, the adhesive flows into the second recessed portion before flowing into the first recessed portion. In this manner, the adhesion film will not easily be formed in the first recessed portion. Furthermore, since the second base plate is provided between the first recessed portion and the third surface, when an adhesive adheres to the third surface, an adhesive applied to the infrared detecting element will not easily flow into the first recessed portion compared to a case where an adhesive is applied directly to the first base plate without using the second base plate.

Application Example 2

In the infrared detecting element according to the above-described application example, a side wall of the second recessed portion is inclined with respect to the fourth surface.

According to this application example, the side wall of the second recessed portion is inclined with respect to the fourth surface. An adhesive forming an adhesion film flows along the fourth surface. Since the side wall is inclined with respect to the fourth surface, the adhesive easily flows from the fourth surface along the side wall when it flows. In this manner, the adhesive easily flows into the second recessed portion, and thus the adhesion film will not easily be formed in the first recessed portion.

Application Example 3

In the infrared detecting element according to the above-described application examples, a plurality of the first recessed portions and a plurality of the infrared detecting portions are provided in the first base plate, and a plurality of the first recessed portions are provided in an area that faces the second recessed portion.

According to this application example, since a plurality of the first recessed portions are provided in an area that faces the single second recessed portion, the area of the second recessed portion can be made greater than that of the first recessed portion. Consequently, it is possible to increase the amount of the adhesive that can flow into the second recessed portion, and thus prevent the adhesive from overflowing from the second recessed portion and entering the first recessed portion. As a result, the adhesion film will not easily be formed in the first recessed portion.

Application Example 4

In the infrared detecting element according to the above-described application examples, the second base plate has a side surface, and has a channel portion between the second recessed portion and the side surface.

According to this application example, the infrared detecting element has the channel portion between the second recessed portion and the side surface of the second base plate. Consequently, an adhesive flowing into the second recessed portion can flow to the side surface of the second base plate through the channel portion. As a result, the second recessed portion will not easily be filled with the adhesive, and the adhesion film will not easily be formed in the first recessed portion.

Application Example 5

In the infrared detecting element according to the above-described application examples, the second base plate has a plurality of the second recessed portions, and has channel portions between the second recessed portions.

According to this application example, the infrared detecting element has the channel portions between the second recessed portions. Consequently, an adhesive flowing into a second recessed portion can flow to other second recessed portions through the channel portions. Thus, even if a large amount of an adhesive flows into a second recessed portion, when the amount of the adhesive flowing into the second recessed portion is small, the adhesive can flow to other second recessed portions in which the amount of the adhesive is small through the channel portions. As a result, the second recessed portion will hardly be filled with the adhesive, and the adhesion film will not easily be formed in the first recessed portion.

Application Example 6

In the infrared detecting element according to the above-described application examples, a bottom portion of the second recessed portion shields a hollow space portion surrounded by the first recessed portion and the second recessed portion from the third surface.

According to this application example, the bottom portion shields the hollow space portion surrounded by the first recessed portion and the second recessed portion from the third surface. Consequently, when an adhesive is applied to the third surface, the adhesive will not flow from the third surface to the first recessed portion. As a result, the adhesion film will not easily be formed in the first recessed portion.

Application Example 7

An electronic device of this application example has a light detecting section that detects infrared rays, and the light detecting section has the infrared detecting element according to the above-described application examples.

According to this application example, the electronic device has the light detecting section that detects infrared rays. The light detecting section has the infrared detecting element according to the above-described application examples. The infrared detecting element according to the above-described application examples is an element having good sensitivity in which the adhesion film will not easily be formed in the first recessed portion. According to this application example, therefore, it is possible to achieve an electronic device that has an infrared detecting element with good sensitivity as the light detecting section.

BRIEF DESCRIPTION OF THE DRAWINGS

Referring now to the attached drawings which form a part of this original disclosure.

DETAILED DESCRIPTION OF EXEMPLARY EMBODIMENTS

Hereinafter, embodiments of an infrared detecting element will be explained with reference to the attached drawings. In each drawing, the scale size of each component is different such that each component has a dimension to be recognized in each drawing.

First Embodiment

In the present embodiment, characteristic examples of the infrared detecting element and a method for assembling the infrared detecting element will be explained with reference to FIG. 1-FIG. 4.
(Infrared Detecting Element)

Figure 1A:
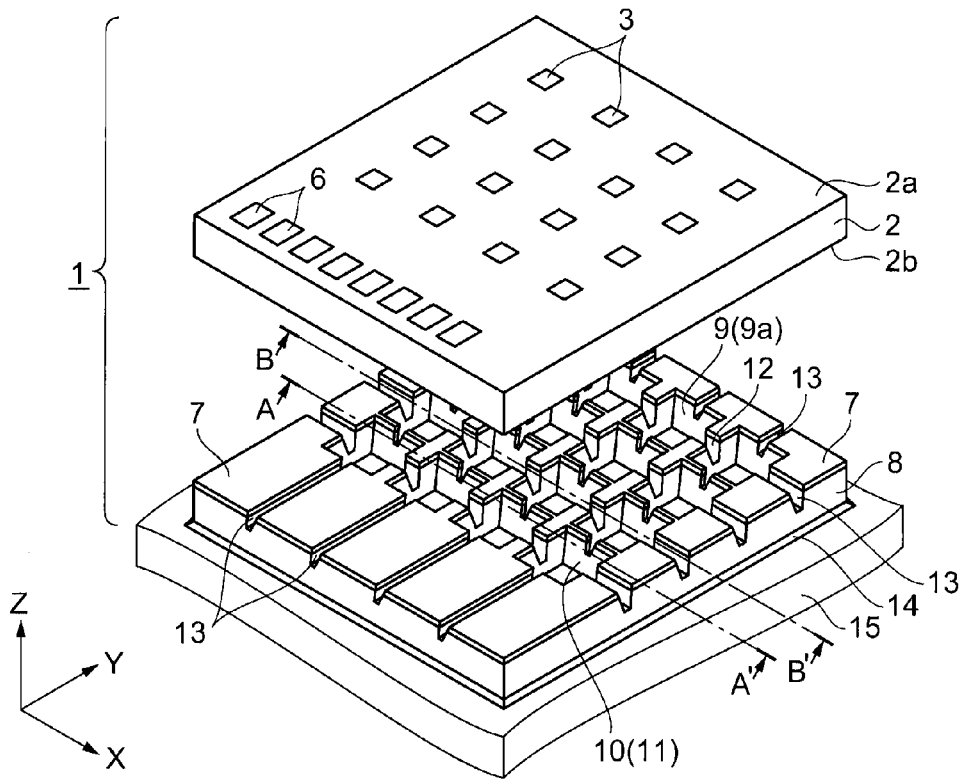
FIG. 1A is a schematic exploded perspective view showing a configuration of an infrared detecting element according to a first embodiment.
Figure 1B:
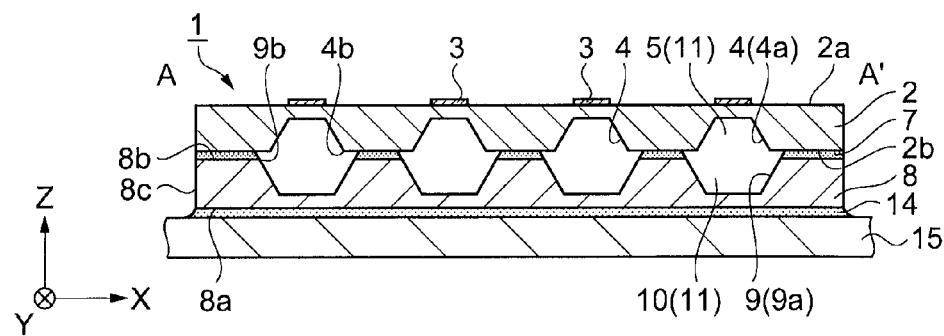
FIG. 1B and FIG. 1C are a cross-sectional diagram of the configuration of the infrared detecting element.
Figure 1C:
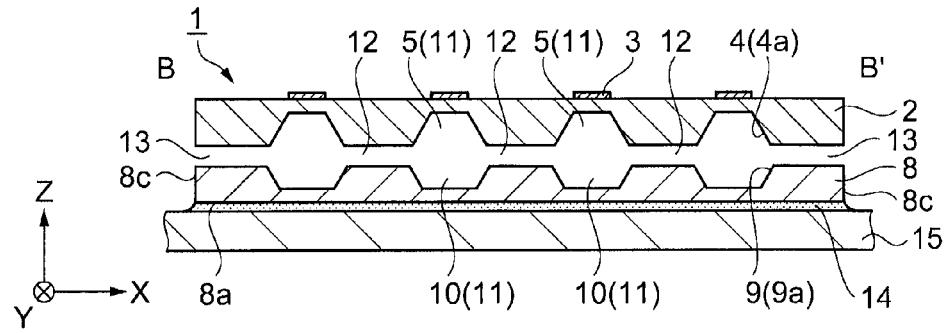

FIG. 1A is a schematic exploded perspective view showing a configuration of the infrared detecting element, and FIG. 1B and FIG. 1C are a cross-sectional diagram of the configuration of the infrared detecting element. FIG. 1B is a cross-sectional diagram along A-A' line of FIG. 1A, and FIG. 1C is a cross-sectional diagram along B-B' line of FIG. 1A. As shown in FIG. 1, the infrared detecting element 1 has a first base plate 2 having a rectangle in a plain view. The directions of two sides of the rectangle of the first base plate 2, which are perpendicular to each other, are referred to as X direction and Y direction. The vertical direction is -Z direction. The surface of the first base plate 2 in Z direction is a first front surface 2a as the first surface, and the surface of the first base plate 2 in -Z direction is a first back surface 2b as the second surface. The first front surface 2a and the first back surface 2b are opposite to each other.

It is sufficient for the material of the first base plate 2 to have rigidity and insulation properties. Silicon, glass, ceramics, reinforced plastics, and the like can be used. When a semiconductor circuit is formed on the first base plate 2, a semiconductor substrate made of silicon and the like is used. In the present embodiment, for example, a semiconductor substrate is used for the first base plate 2.

Sixteen infrared detecting sections 3 are provided on the first front surface 2a of the first base plate 2 in a matrix pattern of four rows and four columns. The infrared detecting section 3 is an element that receives infrared rays and outputs electrical signals corresponding to the amount of received light. In the first back surface 2b, a first recessed portion 4 is provided in an area that opposes each of the infrared detecting sections 3. One first recessed portion 4 is formed with respect to one infrared detecting section 3. Thus, the thickness of the first base plate 2 is small in the area where the infrared detecting sections 3 are provided.

When irradiated by infrared rays, the infrared detecting sections 3 detect the amount of a temperature rise. When heat is hard to transfer from the infrared detecting sections 3, the infrared detecting sections 3 can detect an irradiation amount of infrared rays with good sensitivity. Since the first base plate 2 is thin in the area where the infrared detecting sections 3 are provided, heat is hard to transfer from the infrared detecting sections 3 to the first base plate 2. A space surrounded by the first recessed portions 4 is a first hollow space portion 5. Air is filled in the first hollow space portion 5. Since the air in the first hollow space portion 5 is hard to flow, the infrared detecting element 1 does not easily release heat of the infrared detecting section 3 to the first hollow space portion 5.

Electrodes 6 are provided in the first front surface 2a in line. The electrode 6 is a terminal that outputs electrical signals corresponding to an irradiation amount of infrared rays detected by the infrared detecting sections 3.

An adhesion film 7 and a second base plate 8 are provided to overlap each other in -Z direction of the first base plate 2. The surface of the second base plate 8 in Z direction is a second back surface 8b as the fourth surface, and the surface of the second base plate 8 in -Z direction is a second front surface 8a as the third surface. The second front surface 8a and the second back surface 8b are opposite to each other. The adhesion film 7 is provided between the first back surface 2b and the second back surface 8b, and bonds the first back surface 2b and the second back surface 8b.

The adhesion film 7 is a film formed by solidifying an adhesive. The adhesive used in the present embodiment can be epoxy-based, urethane-based, acrylic-based, silicone-based, polyester-based, imide-based, polyamide-imide based, and the like. Further, an additive such as a thermal hardening initiator can be added.

In the second base plate 8, a second recessed portion 9 is formed in an area of the second back surface 8b that opposes the first recessed portion 4. A space surrounded by the second recessed portion 9 is a second hollow space portion 10, and air is filled in the second hollow space portion 10. Since the air in the second hollow space portion 10 is hard to flow, the infrared detecting element 1 can prevent heat of the infrared detecting section 3 from being released to the second base plate 8.

The second hollow space portion 10 and the first hollow space portion 5 form a hollow space portion 11. The second hollow space portion 10 is formed such that the volume of the second hollow space portion 10 is greater than that of the first hollow space portion 5. A side wall 4a of the first recessed portion 4 is inclined with respect to the first back surface 2b, and a side wall 9a of the second recessed portion 9 is inclined with respect to the second back surface 8b. An area where the side wall 4a of the first recessed portion 4 intersects with the first back surface 2b is a first outer peripheral portion 4b, and an area where the side wall 9a of the second recessed portion 9 intersects with the second back surface 8b is a second outer peripheral portion 9b. The first outer peripheral portion 4b is located inside with respect to the second outer peripheral portion 9b, and the first outer peripheral portion 4b is provided to be surrounded by the second outer peripheral portion 9b.

The adhesion film 7 is a liquid adhesive having viscosity before solidified. When pressure is applied to the adhesive, the adhesive flows into the hollow space portion 11. In this instance, the adhesive contacts the second outer peripheral portion 9b before contacting the first outer peripheral portion 4b. The adhesive then flows into the second recessed portion 9 along the side wall 9a. Consequently, since the adhesive flows into the second recessed portion 9, the adhesion film 7 will not easily be formed in the first recessed portion 4.

The side wall 9a is inclined with respect to the second back surface 8b. Therefore, the adhesion film 7 flowing into the hollow space portion 11 easily flows along the side wall 9a. Consequently, the adhesion film 7 flows into the second recessed portion 9, and does not easily adhere to the first recessed portion 4. Also, since the volume of the second hollow space portion 10 is greater than that of the first hollow space portion 5, the adhesive does not easily fill the second recessed portion 9. Consequently, the adhesion film 7 will not easily be formed in the first recessed portion 4.

Channel portions between recessed portions 12 as the channel portions are formed between the neighboring second recessed portions 9 in the second base plate 8. The channel portions between recessed portions 12 connect the second hollow space portions 10 in the second recessed portions 9. When an adhesive that is a raw material of the adhesion film 7 stands in one second hollow space portion 10, the adhesive can move to the neighboring second hollow space portions 10 by flowing through the channel portions between recessed portions 12. Consequently, the adhesive does not easily fill the second hollow space portion 10, and the adhesion film 7 will not easily be formed in the first recessed portion 4.

In the second recessed portion 9 close to a side surface 8c of the second base plate 8, an outside connecting channel portion 13 as the channel portion is formed between the second recessed portion 9 and the side surface 8c. The outside connecting channel portion 13 connects the second hollow space portion 10 in the second recessed portion 9 and outer air that contacts the side surface 8c. When an adhesive that is a raw material of the adhesion film 7 stands in one second hollow space portion 10, the adhesive can move outside the infrared detecting element 1 from the side surface 8c by flowing through the outside connecting channel portion 13. Consequently, the adhesive does not easily fill the second hollow space portion 10, and the adhesion film 7 will not easily be formed in the first recessed portion 4.

A mounting substrate 15 is provided on the second front surface 8a of the second base plate 8 through an adhesive film 14. Various kinds of circuits are formed on the mounting substrate 15, and the circuits on the mounting substrate 15 and the electrodes 6 are electrically connected. It is thus possible to output signals of an irradiation amount of infrared rays detected by the infrared detecting section 3.

Figure 2A:
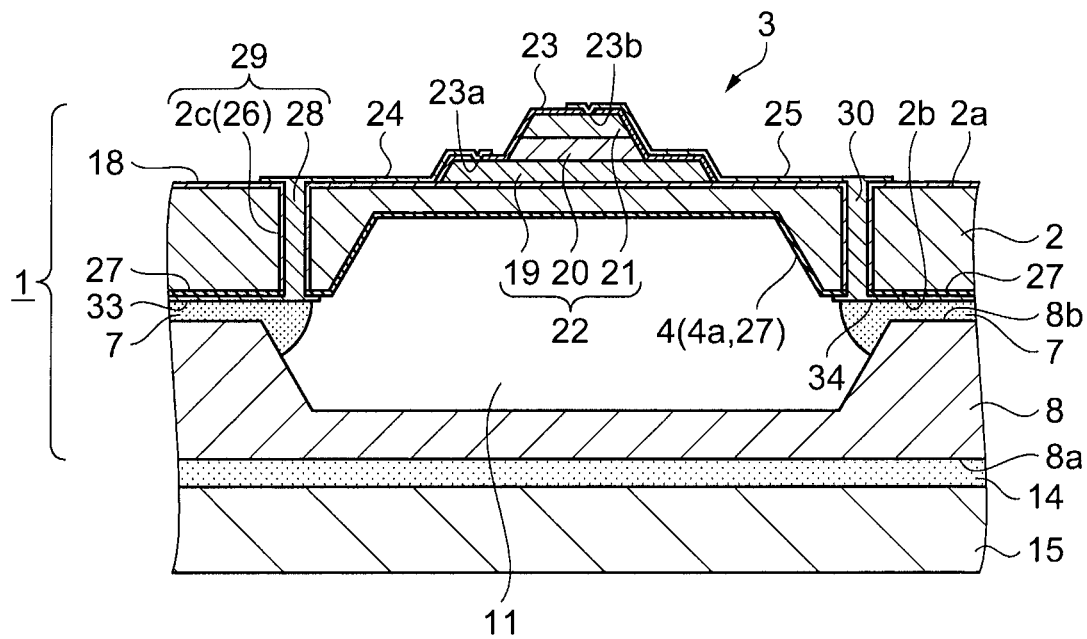
FIG. 2A is a sectional side diagram showing the main part of a configuration of an infrared detecting section.
Figure 2B:
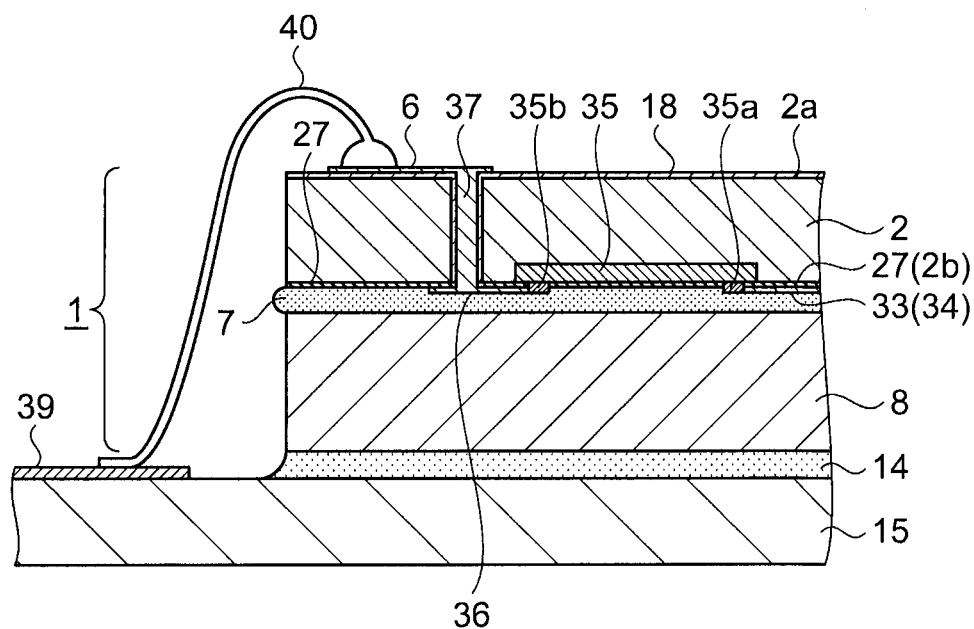
FIG. 2B is a sectional side diagram showing the main part of a configuration of an electrode and a wiring.

FIG. 2A is a sectional side diagram showing the main part of a configuration of the infrared detecting section, and FIG. 2B is a sectional side diagram showing the main part of a configuration of the electrode and the wiring. As shown in FIG. 2A, a first insulating film 18 is formed on the first front surface 2a of the first base plate 2. The first insulating film 18 is an oxide film obtained by oxidizing the first base plate 2 made of silicon, and has electrical insulating properties.

A lower electrode 19 is provided in an area on the first insulating film 18 that opposes the first recessed portion 4, and a pyroelectric body 20 is provided so as to overlap the lower electrode 19. An upper electrode 21 is provided on the pyroelectric body 20. A capacitor 22 is constructed of the lower electrode 19, the pyroelectric body 20, the upper electrode 21, and the like. The polarization amount of the capacitor 22 changes based on the temperature.

A second insulating film 23 is provided so as to cover the capacitor 22. A first contact hole 23a that connects to the lower electrode 19 and a second contact hole 23b that connects to the upper electrode 21 are formed in the second insulating film 23. A first wiring 24 and a second wiring 25 are provided on the first insulating film 18 and the second insulating film 23. The first wiring 24 is connected to the lower electrode 19 through the first contact hole 23a. Likewise, the second wiring 25 is connected to the upper electrode 21 through the second contact hole 23b. The infrared detecting section 3 is constructed of the first insulating film 18, the capacitor 22, the second insulating film 23, the first wiring 24, the second wiring 25, and the like. An infrared absorbing member can be provided so as to overlap the capacitor 22. With this, the sensitivity of the infrared detecting element 1 can further be improved.

A via hole 2c is formed in the first base plate 2, and a third insulating film 26 is formed on the side wall inside the via hole 2c. A fourth insulating film 27 is formed in the first back surface 2b and the first recessed portion 4. The third insulating film 26 and the fourth insulating film 27 are formed by heating and oxidizing. A conductive body 28 is provided inside the via hole 2c, and a penetrating electrode is constructed of the via hole 2c and the conductive body 28. One infrared detecting section 3 has two penetrating electrodes. One penetrating electrode is a first penetrating electrode 29 that connects to the first wiring 24, and the other penetrating electrode is a second penetrating electrode 30 that connects to the second wiring 25.

In the first back surface 2b, a back surface first wiring 33 that connects to the first penetrating electrode 29 is formed, and a back surface second wiring 34 that connects to the second penetrating electrode 30 is formed. The back surface first wiring 33 is connected to the lower electrode 19 through the first penetrating electrode 29 and the first wiring 24. The back surface second wiring 34 is connected to the upper electrode 21 through the second penetrating electrode 30 and the second wiring 25. Consequently, the polarization amount of the capacitor 22 can be detected through the back surface first wiring 33 and the back surface second wiring 34.

As shown in FIG. 2B, an integrated circuit 35 is formed on the first back surface 2b of the first base plate 2. The integrated circuit 35 includes a drive circuit that drives the infrared detecting section 3, a control circuit that switches the output of the plurality of the infrared detecting sections 3, and the like. The integrated circuit 35 is provided with a plurality of input terminals 35a and output terminals 35b. The back surface first wiring 33 and the back surface second wiring 34 are connected to the input terminals 35a. A back surface third wiring 36 is provided so as to be connected to the output terminals 35b.

A third penetrating electrode 37 that penetrates the first base plate 2 is formed so as to connect to the back surface third wiring 36. The third penetrating electrode 37 has a structure similar to the first penetrating electrode 29. The electrodes 6 are provided on the first front surface 2a so as to connect to the third penetrating electrode 37.

A wiring 39 is provided on a surface of the mounting substrate 15 on which the infrared detecting element 1 is provided. The electrodes 6 and the wiring 39 are connected by a bonding wire 40. With this, electrical signals that the integrated circuit 35 outputs to the output terminals 35b are output to the wiring 39 through the back surface third wiring 36, the third penetrating electrode 37, the electrodes 6, and the bonding wire 40.

(Method for Assembling Infrared Detecting Element)

Figure 3A:
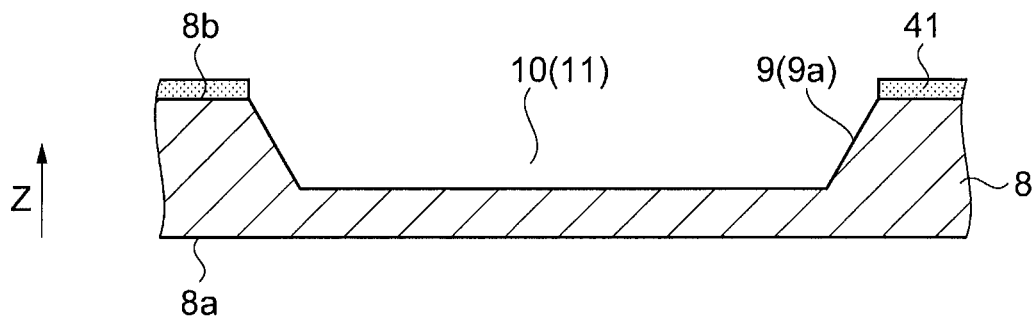
FIG. 3 is a diagram explaining a method for assembling the infrared detecting element.

A method for assembling the infrared detecting element will be explained with reference to FIG. 3 and FIG. 4. FIG. 3 and FIG. 4 is a diagram explaining the method for assembling the infrared detecting element. As shown in FIG. 3A, the second base plate 8 is prepared. The second recessed portion 9 is formed in the second base plate 8. The second recessed portion 9 can be formed by a photolithography method or an etching method. The forming method is well-known, and will not be explained.

Next, an adhesive 41 is applied to the second back surface 8b. The adhesive 41 is a material that becomes the adhesive film 7 when solidified. Preferably, the adhesive 41 has good wettability and low viscosity. The adhesion film 7 can be formed in all the area to be bonded by spreading the adhesive 41. As the method for applying the adhesive 41, it is possible to use a printing method such as screen printing, relief printing, offset printing, an ink-jet method, or an application method for using a syringe. In the present embodiment, the adhesive 41 is applied, for example, by using an ink-jet method.

Figure 3B:
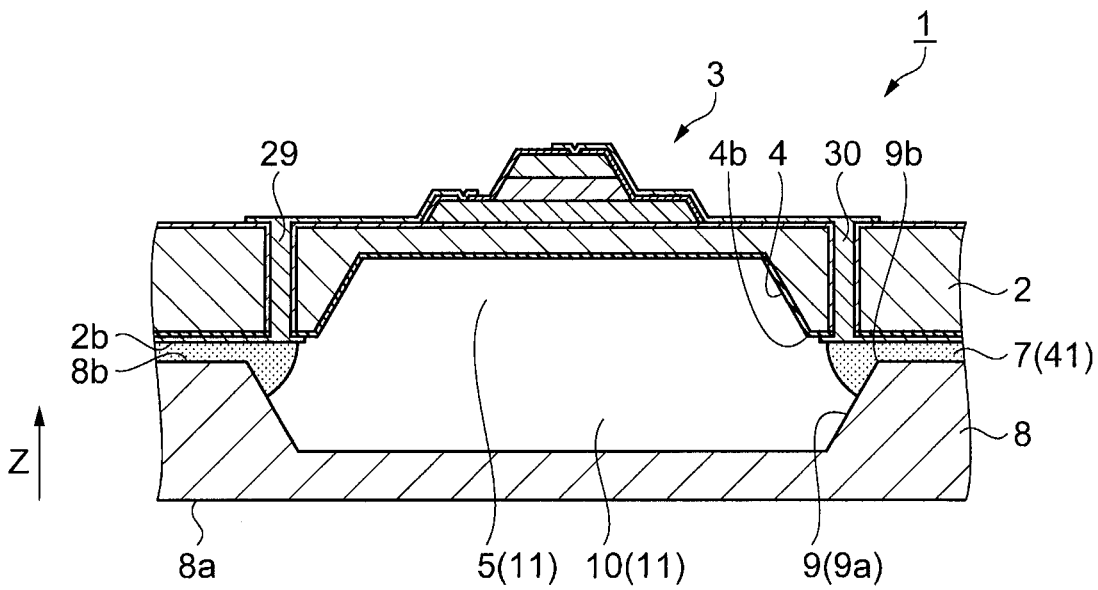

Next, as shown in FIG. 3B, the first base plate 2 is prepared. The first hollow space portion 5, the first penetrating electrode 29, the second penetrating electrode 30, the infrared detecting section 3, and various kinds of wirings are formed in the first base plate 2. The third penetrating electrode 37 is formed in an area of the first base plate 2 that is not shown in the drawing. These components can be formed by a film adhesion method such as a sputtering method or a vapor-deposition method, a photolithography method, or an etching method. The forming method is well-known, and will not be explained.

Next, the first base plate 2 is provided so as to overlap the second base plate 8 by attaching the first back surface 2b and the second back surface 8b in which the adhesive 41 is applied. The adhesive 41 is sandwiched by the second base plate 8 and the first base plate 2, and thereby pressurized. The adhesive 41 then flows into the hollow space portion 11. In this instance, since the second outer peripheral portion 9b is located in a position that surrounds the first outer peripheral portion 4b, the adhesive 41 reaches the second outer peripheral portion 9b before reaching the first outer peripheral portion 4b. The side wall 9a is connected to the second outer peripheral portion 9b, and the side wall 9a is inclined with respect to the second back surface 8b. The gravity and surface tension acting on the adhesive 41 cause the adhesive 41 to flow along the side wall 9a toward the second recessed portion 9. As a result, the adhesive 41 does not easily adhere to the first recessed portion 4.

Next, the adhesive 41 is solidified by heating and drying the second base plate 8 and the first base plate 2. The adhesive then becomes the adhesion film 7, and the second base plate 8 and the first base plate 2 are bonded. In this manner, the infrared detecting element 1 is completed.

Figure 3C:
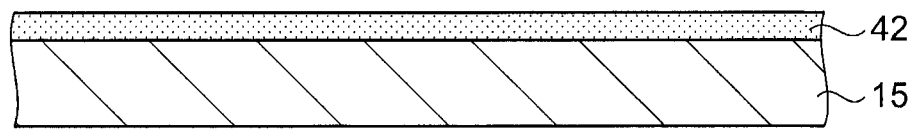

Next, as shown in FIG. 3C, the mounting substrate 15 is prepared, and an adhesive 42 is applied to an area of the mounting substrate 15 where the infrared detecting element 1 is to be provided. The adhesive 42 is a material that becomes the adhesive film 14 when solidified. The method for applying the adhesive 42 is not limited to a particular one, and a method similar to the method for applying the adhesive 41 can be used.

Figure 4A:
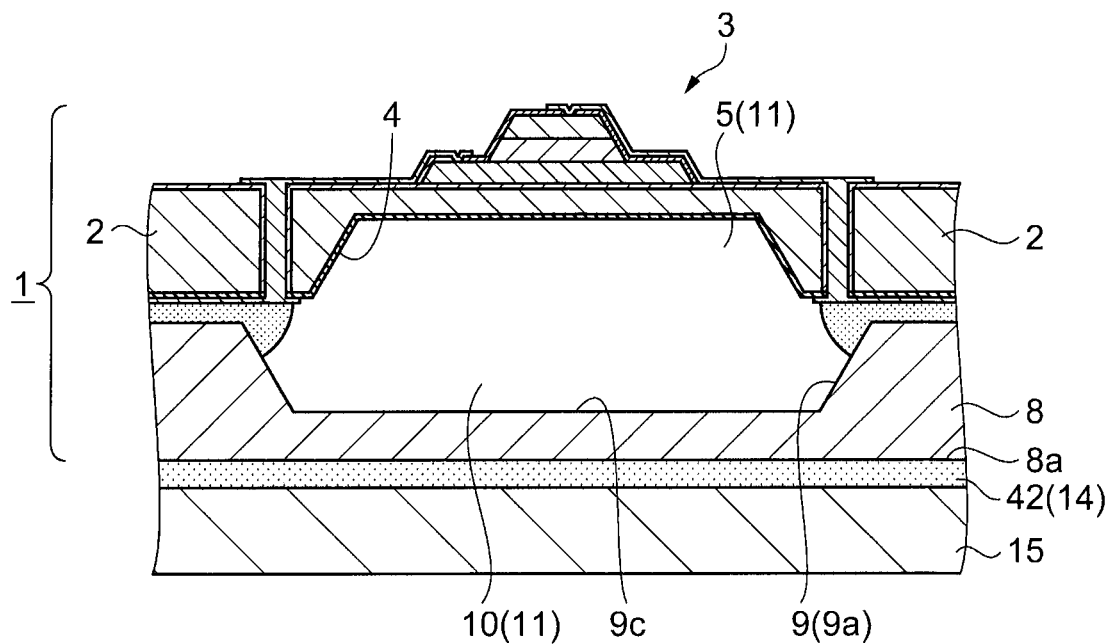
FIG. 4 is a diagram explaining a method for assembling the infrared detecting element.

Next, as shown in FIG. 4A, the infrared detecting element 1 is provided so as to overlap the adhesive 42. The mounting substrate 15, on which the infrared detecting element 1 has been provided, is heated and dried so as to solidify the adhesive 42. Consequently, the adhesive 42 becomes the adhesion film 14, and the infrared detecting element 1 is fixed to the mounting substrate 15.

In the second base plate 8, a bottom portion 9c that is the bottom of the second recessed portion 9 shields the hollow space portion 11. Thus, when the adhesive 42 is applied to the second front surface 8a, the adhesive 42 does not flow from the second front surface 8a to the first recessed portion 4. Consequently, the adhesion film 14 will not easily be formed in the first recessed portion 4.

Figure 4B:
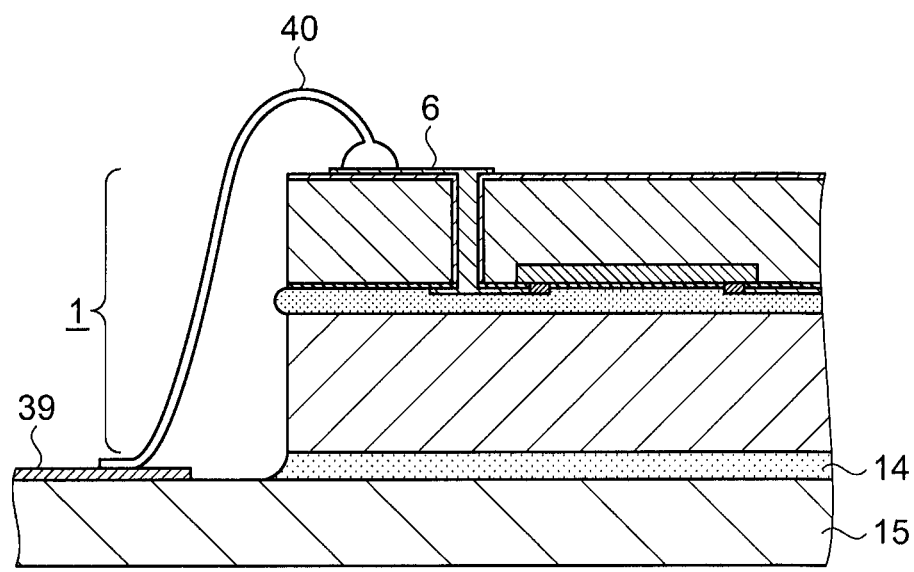

Next, as shown in FIG. 4B, the electrodes 6 on the infrared detecting element 1 and the wiring 39 on the mounting substrate 15 are connected by the bonding wire 40. The bonding method using the bonding wire 40 is well-known, and will not be explained. By the above-described processes, the infrared detecting element 1 is assembled and mounted on the mounting substrate 15.

As described above, the present embodiment has the following effects:

(1) According to the present embodiment, since the second outer peripheral portion 9b surrounds the first outer peripheral portion 4b, the adhesive 41 flows into the second recessed portion 9 before flowing into the first recessed portion 4. Consequently, the adhesion film 7 will not easily be formed in the first recessed portion 4.

(2) According to the present embodiment, the second base plate 8 is provided between the first recessed portion 4 and the second front surface 8a, and the bottom portion 9c shields the hollow space portion 11. Thus, when the adhesive 42 adheres to the second front surface 8a to mount the infrared detecting element 1, the adhesive 42 will not flow from the second front surface 8a into the hollow space portion 11. As a result, the adhesive 42 can be prevented from adhering to the first recessed portion 4.

(3) According to the present embodiment, the side wall 9a of the second recessed portion 9 is inclined with respect to the second back surface 8b. The adhesive 41 easily flows along the inclined surface when it flows. Consequently, since the adhesive 41 flows into the second recessed portion 9 rather than into the first recessed portion 4, the adhesion film will not easily be formed in the first recessed portion 4.

(4) According to the present embodiment, the outside connecting channel portion 13 is provided between the second recessed portion 9 and the side surface 8c of the second base plate 8. The adhesive 41 flowing into the second recessed portion 9 can move to the side surface 8c of the second base plate 8 by flowing through the outside connecting channel portion 13. As a result, since the second recessed portion 9 is not easily filled with the adhesive 41, the adhesion film will not easily be formed in the first recessed portion 4.

(5) According to the present embodiment, the channel portions between recessed portions 12 are provided so as to connect the plurality of second recessed portions 9. The adhesive 41 flowing into a second recessed portion 9 can move to other second recessed portions 9 by flowing through the channel portions. As a result, since the second recessed portion 9 is not easily filled with the adhesive 41, the adhesion film will not easily be formed in the first recessed portion 4.

(6) According to the present embodiment, the channel portions between recessed portions 12 and the outside connecting channel portion 13 connect each hollow space portion 11 with outer air. It is thus possible to prevent the pressure of the hollow space portion 11 from increasing even when gas is generated in the process where the adhesive 41 is solidified and becomes the adhesion film 7. Consequently, the thickness of the adhesion film 7 can be made uniform. The speed of transmitting heat from the first base plate 2 to the second base plate 8 can be made identical by making the thickness of the adhesion film 7 uniform. As a result, it is possible to reduce the dispersion of the sensitivity of the infrared detecting section 3 for detecting infrared rays.

Second Embodiment

Next, another embodiment of the infrared detecting element will be explained with reference to a sectional side diagram showing the main part of a configuration of the infrared detecting element of FIG. 5. The present embodiment is different from the first embodiment in the shape of the second recessed portion 9 shown in FIG. 1B. The same points as the first embodiment will not be explained.

Figure 5:
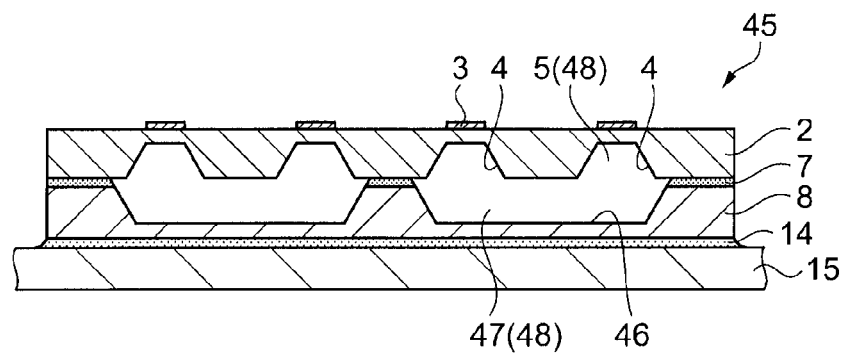
FIG. 5 is a sectional side diagram showing the main part of a configuration of an infrared detecting element according to a second embodiment.

In the present embodiment, as shown in FIG. 5, the infrared detecting element 45 has the first base plate 2, and the plurality of infrared detecting sections 3 are provided in the first base plate 2. The first base plate 2 and the second base plate 8 are bonded by the adhesion film 7. One first recessed portion 4 is provided in the first base plate 2 corresponding to one infrared detecting section 3. One second recessed portion 46 is provided in the second base plate 8 corresponding to two first recessed portions 4. One hollow space portion 48 is formed by the first hollow space portions 5 surrounded by the first recessed portions 4 and a second hollow space portion 47 surrounded by the second recessed portion 46. Accordingly, the number of the infrared detecting sections 3 and the number of the first recessed portions 4 are the same, and the number of the second recessed portions 46 is smaller than the number of the infrared detecting sections 3. One second recessed portion 46 can be formed with respect to three or more first recessed portion 4 in the second base plate 8. The pattern of the second base plate 8 can be made simple, and thus the shape of the second base plate 8 can easily be checked.

As described above, the present embodiment has the following effects:

(1) According to the present embodiment, since the plurality of first recessed portions 4 are provided so as to oppose one second recessed portion 46. The area of the second recessed portion 46 thus can be made greater than that of the first recessed portion 4. Consequently, the second recessed portion 46 is not easily filled with the adhesive 41 even if the adhesive 41 flows into the second recessed portion 46, and thus the adhesive 41 will not easily adhere to the first recessed portion 4.

(2) According to the present embodiment, the number of the second recessed portions 46 is smaller than the number of the second recessed portions 9 of the first embodiment. Consequently, the shape of the pattern for etching the second base plate 8 can be made simple, and the yield of the second base plate 8 can be improved. As a result, the second base plate 8 can be manufactured with good productivity.

Third Embodiment

Figure 6:
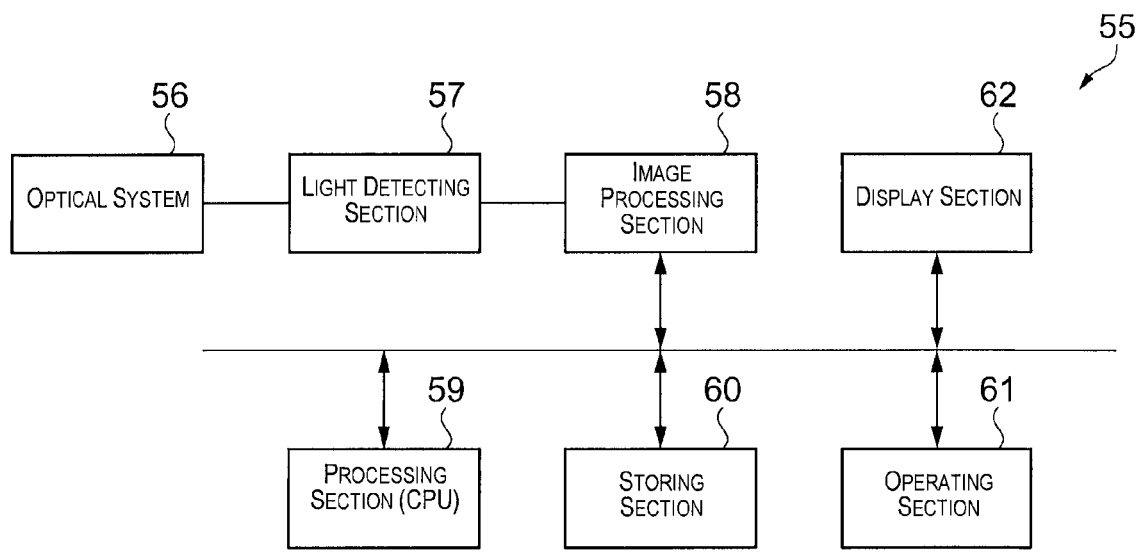
FIG. 6 is a block diagram showing a configuration of an infrared camera according to a third embodiment.

Next, an embodiment of an infrared camera that is one of the electronic devices provided with the infrared detecting element as its infrared detecting section will be explained with reference to a block diagram showing a configuration of the infrared camera of FIG. 6. As shown in FIG. 6, the infrared camera 55 as the electronic device includes an optical system 56, a light detecting section 57, an image processing section 58, a processing section 59, a storing section 60, an operating section 61, and a display section 62.

The optical system 56 includes, for example, a single or a plurality of lenses, and a driving section that drives the lens. The optical system 56 forms an image of an object onto the light detecting section 57. The optical system 56 also conducts focus adjustment as needed.

In the light detecting section 57, the infrared detecting element 1 or the infrared detecting element 45 of the above embodiments is used. In addition to the detectors that are two-dimensionally aligned, the light detecting section 57 can include a row selection circuit (row driver), a readout circuit that reads out data from the detectors through column lines, an A/D converting section, and the like. By sequentially reading out data from the respective detectors that are two-dimensionally aligned, an image data of an object can be formed.

The image processing section 58 conducts various kinds of image processing such as image correction processing based on digital image data (pixel data) from the light detecting section 57.

The processing section 59 controls the entire infrared camera 55, and controls each block in the infrared camera 55. The processing section 59 can be implemented by, for example, a CPU and the like. The storing section 60 stores various kinds of information, and functions as a work area for the processing section 59 or the image processing section 58, for example. The operating section 61 serves as an interface, so that a user can operate the infrared camera 55. The operating section 61 can be implemented by, for example, various kinds of buttons or a GUI (Graphical User Interface) screen. The display section 62 displays images obtained by the light detecting section 57 or a GUI screen, for example. The display section 62 can be implemented by various kinds of displays such as a liquid crystal display or an organic EL display.

In this manner, thermal (optical) distribution images can be provided by using the light detecting section 57 in which the infrared detecting sections 3 are two-dimensionally aligned in two orthogonal axis directions. Electronic devices such as a thermography, an in-vehicle night vision, or a monitoring camera can be constructed by using the light detecting section 57.

Various kinds of electronic devices can be constructed by using one cell or a plurality of cells of the infrared detecting sections 3 as a sensor, and examples of such electronic devices include an analyzing device (measuring device) that analyzes (measures) physical information of an object, a security device that detects fire or heat generation, and an FA (Factory Automation) machine that is provided in a factory and the like.

As described above, the present embodiment has the following effect:

(1) According to the present embodiment, the infrared camera 55 has the light detecting section 57, and the infrared detecting element 1 or the infrared detecting element 45 is used in the light detecting section 57. Since the infrared detecting element 1 or the infrared detecting element 45 used in the light detecting section 57 can detect infrared rays with good sensitivity, the infrared camera 55 can serve as an electronic device provided with the infrared detecting element that can detect infrared rays with good sensitivity.

Fourth Embodiment

Figure 7:
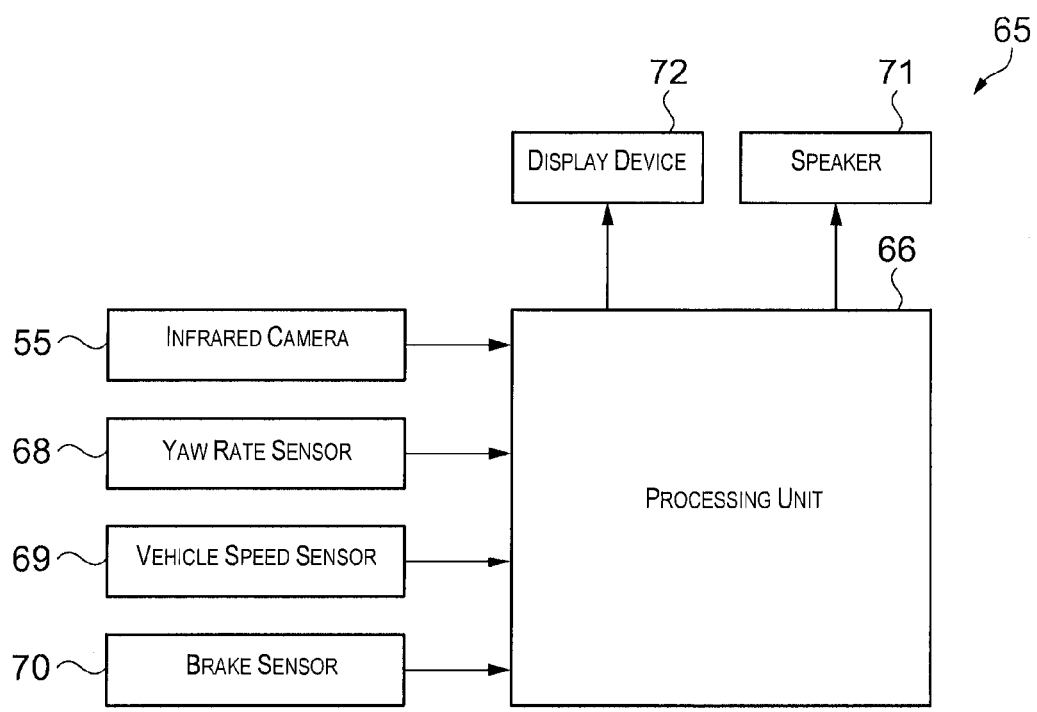
FIG. 7 is a block diagram showing a configuration of a driving support device according to a fourth embodiment.

Next, an embodiment of a driving support device that is one of the electronic devices using the infrared camera provided with the infrared detecting element in its infrared detecting section will be explained with reference to FIG. 7 and FIG. 8. FIG. 7 is a block diagram showing a configuration of the driving support device, and FIG. 8 is a schematic perspective view showing a vehicle in which the driving support device is installed.

As shown in FIG. 7, the driving support device 65 as the electronic device has a processing unit 66 provided with a CPU for controlling the driving support device 65, the infrared camera 55 that can detect infrared rays with respect to a predetermined imaging region outside the vehicle, a yaw rate sensor 68 that detects the yaw rate of the vehicle, a vehicle speed sensor 69 that detects the running speed of the vehicle, a brake sensor 70 that detects whether or not the driver operates the brake, a speaker 71, and a display device 72. The infrared camera 55 in the present embodiment is the same camera as the infrared camera 55 in the above-described embodiment.

The processing unit 66 of the driving support device 65 detects an object such as a thing or a pedestrian that is present ahead in the running direction of the vehicle based on infrared images of the vicinity of the vehicle obtained by taking images with the infrared camera 55, and detection signals with respect to the running state of the vehicle detected by the respective sensors 68-70, for example. When the processing unit 66 of the driving support device 65 judges that the detected object and the vehicle are likely to collide, it causes the speaker 71 or the display device 72 to output an alarm.

Figure 8:
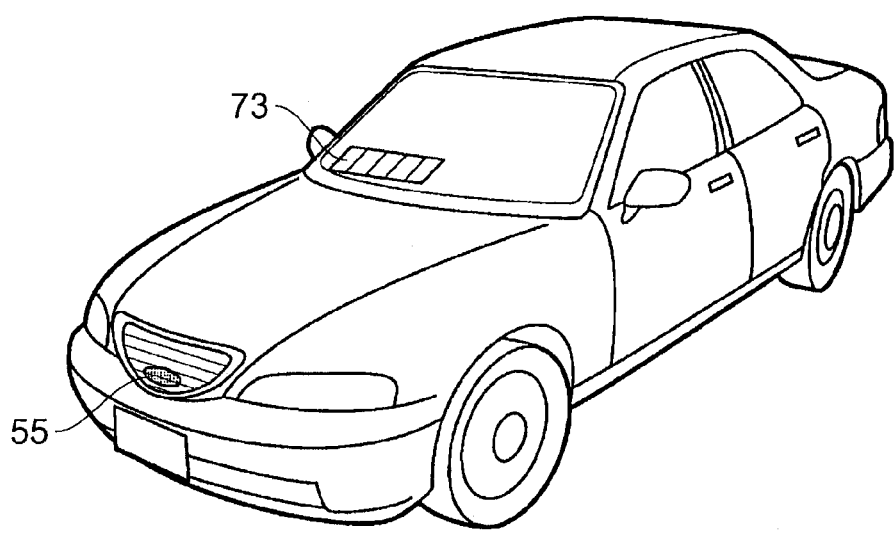
FIG. 8 is a schematic perspective view showing a vehicle in which the driving support device is installed.

As shown in FIG. 8, the infrared camera 55 is provided in the vicinity of the center of the front portion of the vehicle in the vehicle width direction. The display device 72 is configured to have an HUD (Head Up Device) 73 that displays various kinds of information in a position that does not hinder the driver's front vision in the front window.

As described above, the present embodiment has the following effect:

(1) According to the present embodiment, the driving support device 65 has the infrared camera 55. The infrared camera 55 has the light detecting section 57, and the infrared detecting element 1 or the infrared detecting element 45 is used in the light detecting section 57. Accordingly, the driving support device 65 can serve as an electronic device having the infrared camera 55 provided with the infrared detecting element that can detect infrared rays with good sensitivity.

Fifth Embodiment

Figure 9:
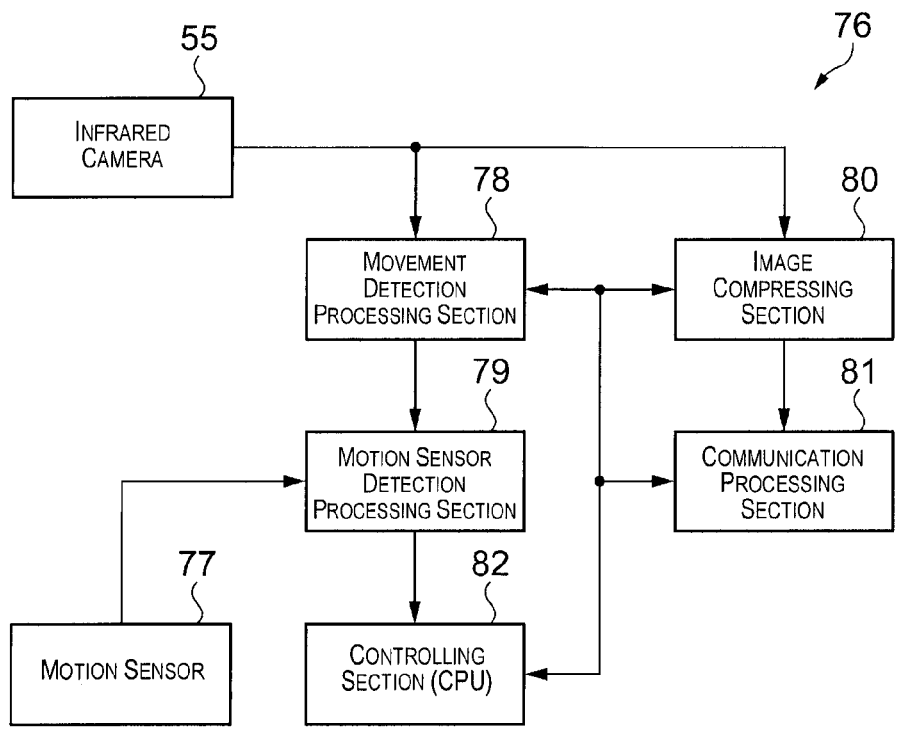
FIG. 9 is a block diagram showing a configuration of a security device according to a fifth embodiment.

Next, an embodiment of a security device that is one of the electronic devices using the infrared camera provided with the infrared detecting element in its infrared detecting section will be explained with reference to FIG. 9 and FIG. 10. FIG. 9 is a block diagram showing a configuration of the security device, and FIG. 10 is a diagram showing a house in which the security device is installed.

As shown in FIG. 9, the security device 76 as the electronic device has the infrared camera 55 that takes images at least of a monitored area, and a motion sensor 77 that detects an intruder in the monitored area. The security device 76 has a movement detection processing section 78 that detects a moving object that enters the monitored area by processing image data output from the infrared camera 55, and a motion sensor detection processing section 79 that conducts detection processing of the motion sensor 77. Further, the security device 76 has an image compressing section 80 that compresses image data output from the infrared camera 55 by a predetermined method, and a communication processing section 81 that receives compressed image data, transmission of intruder detection information, or various kinds of setting information from external devices to the security device 76. Furthermore, the security device 76 has a controlling section 82 that conducts condition setting, processing command transmission, response processing to the respective processing section by using a CPU. The infrared camera 55 in the present embodiment is the same camera as the infrared camera 55 in the above-described embodiment.

The movement detection processing section 78 has a buffer memory, a block data smoothing section to which the output of the buffer memory is input, and a state change detecting section to which the output of the block data smoothing section is input. These are not shown in the drawings. The state change detecting section of the movement detection processing section 78 detects change in state by using the fact that image data is the same even between different frames taken as moving image if the monitored area is in rest state, but difference occurs in the image data between frames if change in state occurs (a moving object enters).

Figure 10:
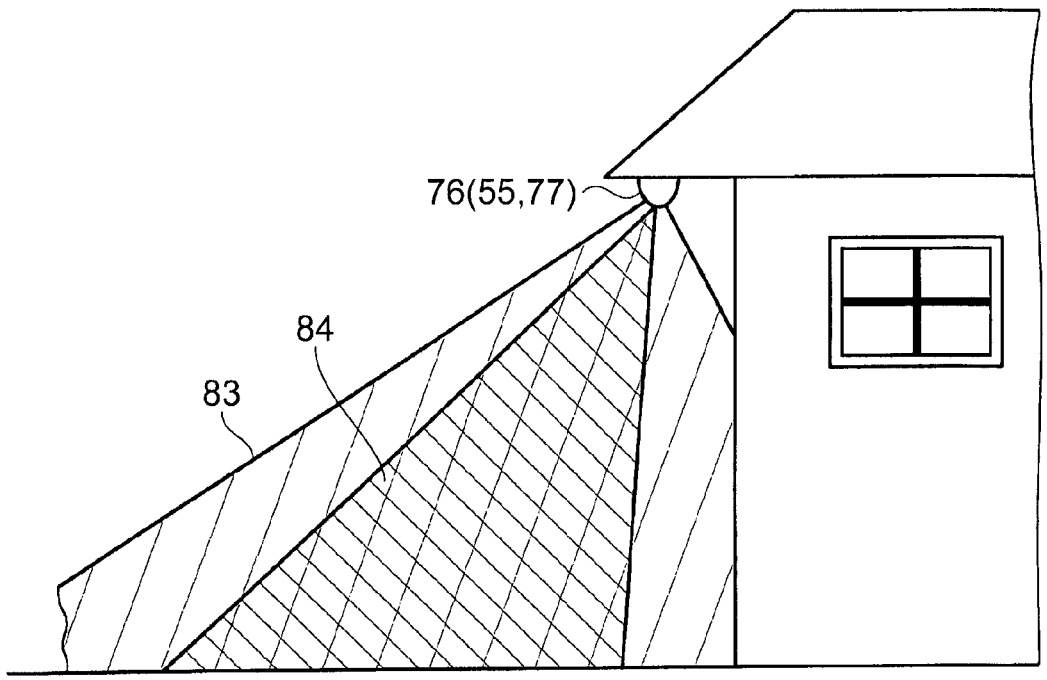
FIG. 10 is a diagram showing a house in which the security device is installed.

As shown in FIG. 10, regarding the security device 76, the infrared camera 55 and the motion sensor 77 are provided under the eaves. The infrared camera 55 detects an image-taking area 83, and the motion sensor 77 detects a detection area 84.

As described above, the present embodiment has the following effect:

(1) According to the present embodiment, the security device 76 has the infrared camera 55. The infrared camera 55 has the light detecting section 57, and the infrared detecting element 1 or the infrared detecting element 45 is used in the light detecting section 57. Accordingly, the security device 76 can serve as an electronic device having the infrared camera 55 provided with the infrared detecting element that can detect infrared rays with good sensitivity.

Sixth Embodiment

Figure 11:
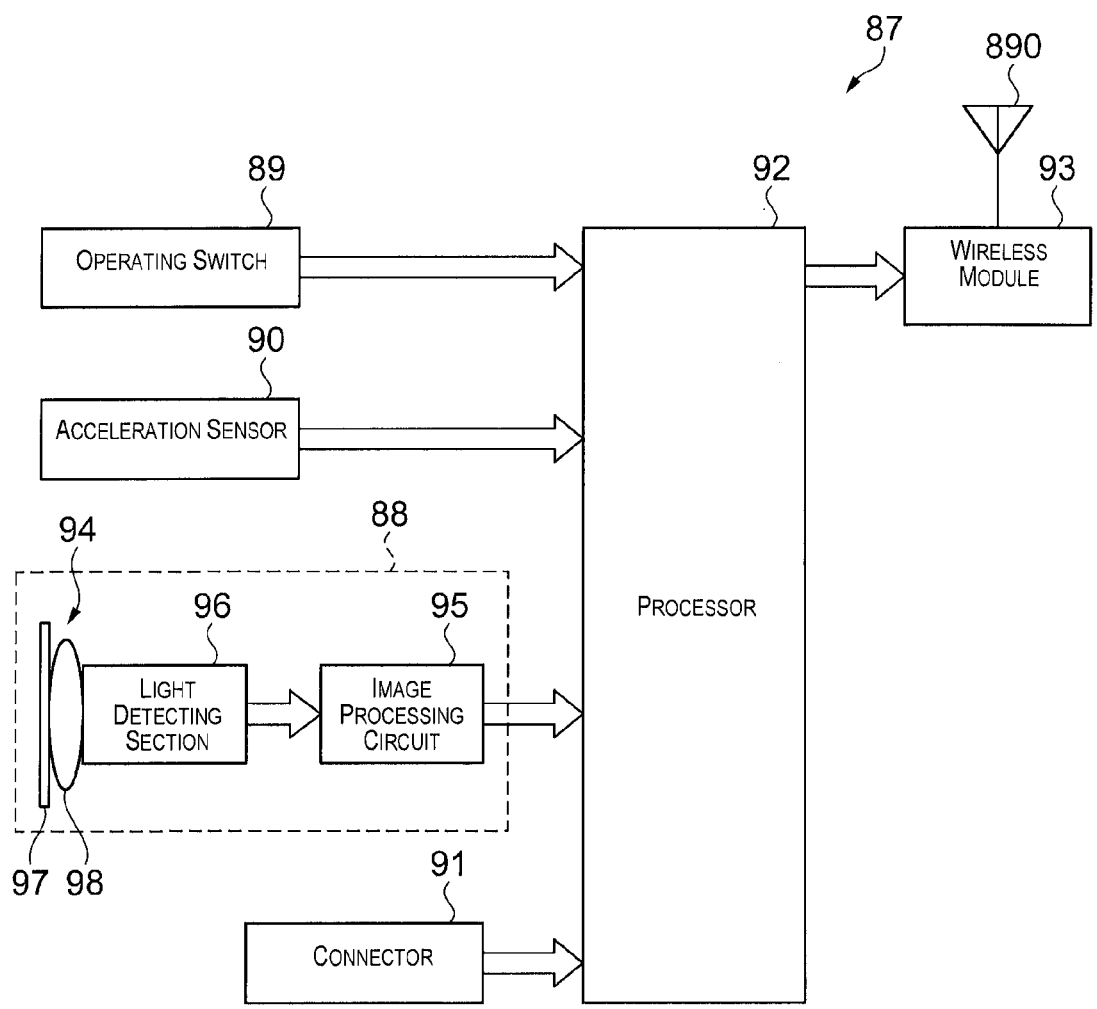
FIG. 11 is a block diagram showing a configuration of a controller for a game device according to a sixth embodiment.
Figure 12:
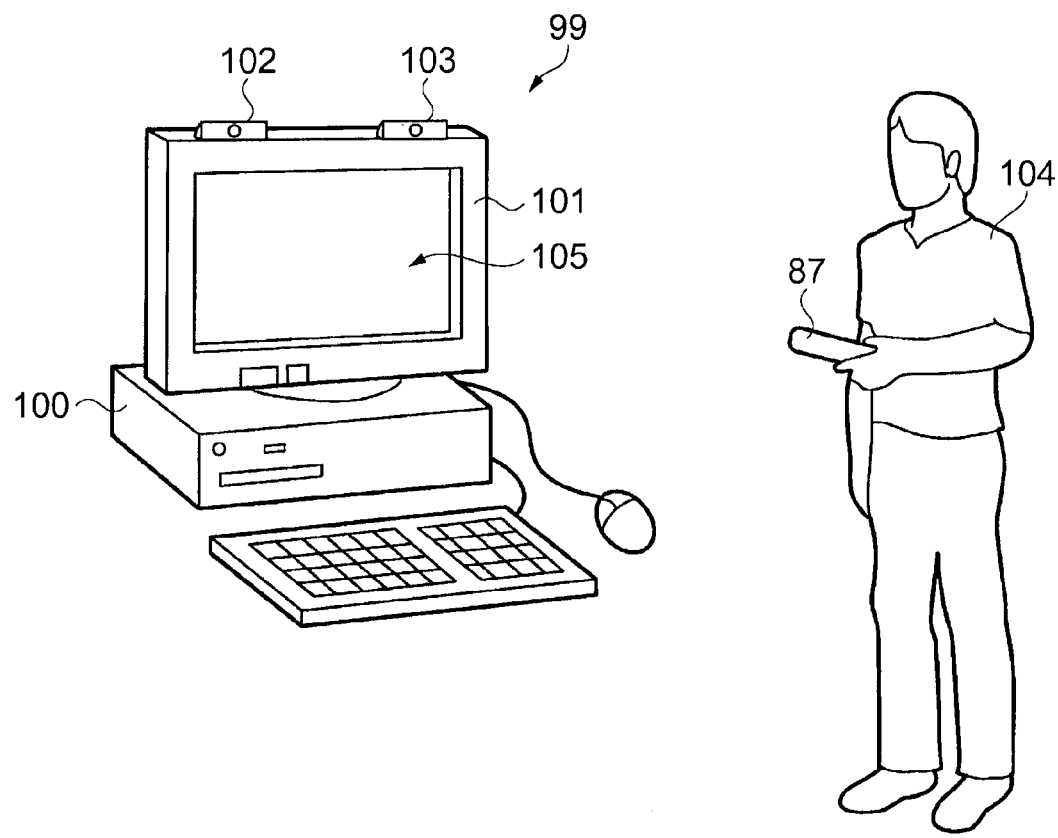
FIG. 12 is a diagram explaining how to use the controller.

Next, an embodiment of a game device that is one of the electronic devices using the infrared camera provided with the infrared detecting element in its infrared detecting section will be explained with reference to FIG. 11 and FIG. 12. FIG. 11 is a block diagram showing a configuration of a controller for the game device, and FIG. 12 is a diagram explaining how to use the controller.

As shown in FIG. 11, the controller 87 as the electronic device used for the game device has an imaging information computing unit 88, an operating switch 89, an acceleration sensor 90, a connector 91, a processor 92, and a wireless module 93.

The imaging information computing unit 88 has an imaging unit 94, and an image processing circuit 95 for processing data of an image taken by the imaging unit 94. The imaging unit 94 includes a light detecting section 96, and an infrared filter 97 that transmits only infrared rays and an optical system 98 such as a lens are provided in front thereof. The image processing circuit 95 processes infrared image data obtained from the imaging unit 94, detects a bright portion, detects the gravity center or the area thereof, and outputs data thereof. The infrared detecting element 1 or the infrared detecting element 45 is used in the light detecting section 96 of the present embodiment.

The processor 92 outputs operation data from the operating switch 89 and acceleration data and bright portion data from the acceleration sensor 90 as a series of control data. The wireless module 93 modulates carrier waves having a predetermined frequency by this control data, and outputs them as radio signals from an antenna 890.

Also, data input through the connector 91 provided in the controller 87 is processed by the processor 92 in the same manner as the above-described data, and output as control data from the wireless module 93 and the antenna 890.

As shown in FIG. 12, the game device 99 has the controller 87, a game device main body 100, a display 101, an LED module 102, and an LED module 103. A player 104 can play a game by holding the controller 87 with one hand. When the imaging unit 94 of the controller 87 is turned to a screen 105 of the display 101, the imaging unit 94 detects infrared rays output from the LED module 102 and the LED module 103 provided in the vicinity of the display 101, and the controller 87 obtains information on the position and the area of the LED module 102 and the LED module 103 as highly bright point information. Data on the position and the size of the bright point is transmitted from the controller 87 to the game device main body 100 wirelessly, and received by the game device main body 100. When the player 104 moves the controller 87, data on the position and the size of the bright point changes. Since the game device main body 100 can obtain operation signals corresponding to the movement of the controller 87 by using this, the game can be conducted accordingly.

As described above, the present embodiment has the following effect:

(1) According to the present embodiment, the controller 87 of the game device 99 has the light detecting section 96, and the infrared detecting element 1 or the infrared detecting element 45 is used in the light detecting section 96. Since the infrared detecting element 1 or the infrared detecting element 45 used in the light detecting section 96 can detect infrared rays with good sensitivity, the game device 99 can serve as an electronic device having the controller 87 provided with the infrared detecting element that can detect infrared rays with good sensitivity.

Seventh Embodiment

Figure 13:
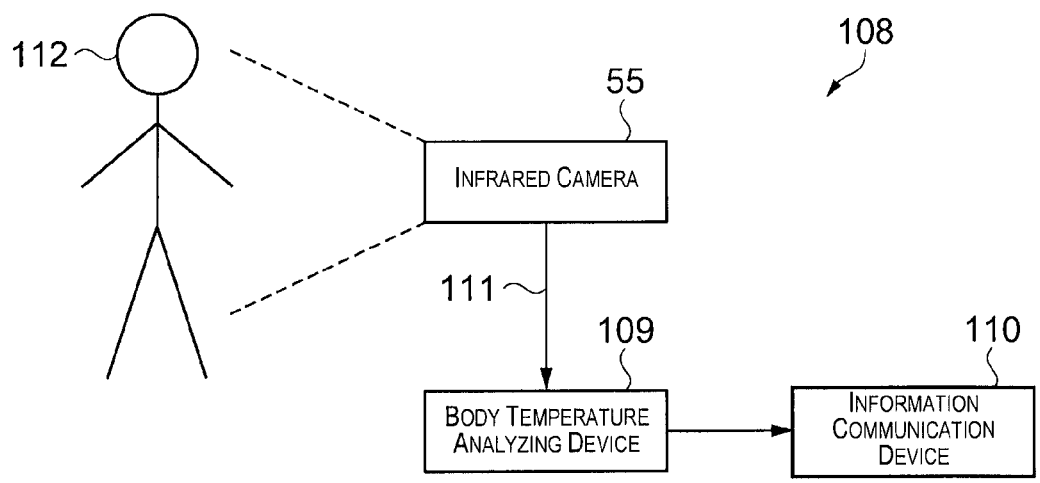
FIG. 13 is a block diagram showing a configuration of a body temperature measuring device according to a seventh embodiment.

Next, an embodiment of a body temperature measuring device that is one of the electronic devices using the infrared camera provided with the infrared detecting element in its infrared detecting section will be explained with reference to FIG. 13. FIG. 13 is a block diagram showing a configuration of the body temperature measuring device.

As shown in FIG. 13, the body temperature measuring device 108 as the electronic device has the infrared camera 55, a body temperature analyzing device 109, an information communication device 110, and a cable 111. The infrared camera 55 in the present embodiment is the same camera as the infrared camera 55 in the third embodiment.

The infrared camera 55 takes images of a predetermined object area, and transmits information on the taken image of an object person 112 to the body temperature analyzing device 109 through the cable 111. The body temperature analyzing device 109 has an image reading processing unit that reads a thermal distribution image from the infrared camera 55, and a body temperature analyzing processing unit that creates a body temperature analyzing table based on data from the image reading processing unit and an image analyzing setting table. The body temperature analyzing device 109 transmits body temperature information transmission data based on the body temperature analyzing table to the information communication device 110. The body temperature information transmission data can include predetermined data corresponding to abnormal body temperature. Also, when it is judged that there are a plurality of object persons 112 in the imaged area, the body temperature information transmission data can include the number of the object persons 112 and the number of persons who have an abnormal body temperature.

As described above, the present embodiment has the following effect:

(1) According to the present embodiment, the body temperature measuring device 108 has the infrared camera 55. The infrared camera 55 has the light detecting section 57, and the infrared detecting element 1 or the infrared detecting element 45 is used in the light detecting section 57. Accordingly, the body temperature measuring device 108 can serve as an electronic device having the infrared camera 55 provided with the infrared detecting element that can detect infrared rays with good sensitivity.

Eighth Embodiment

Figure 14:
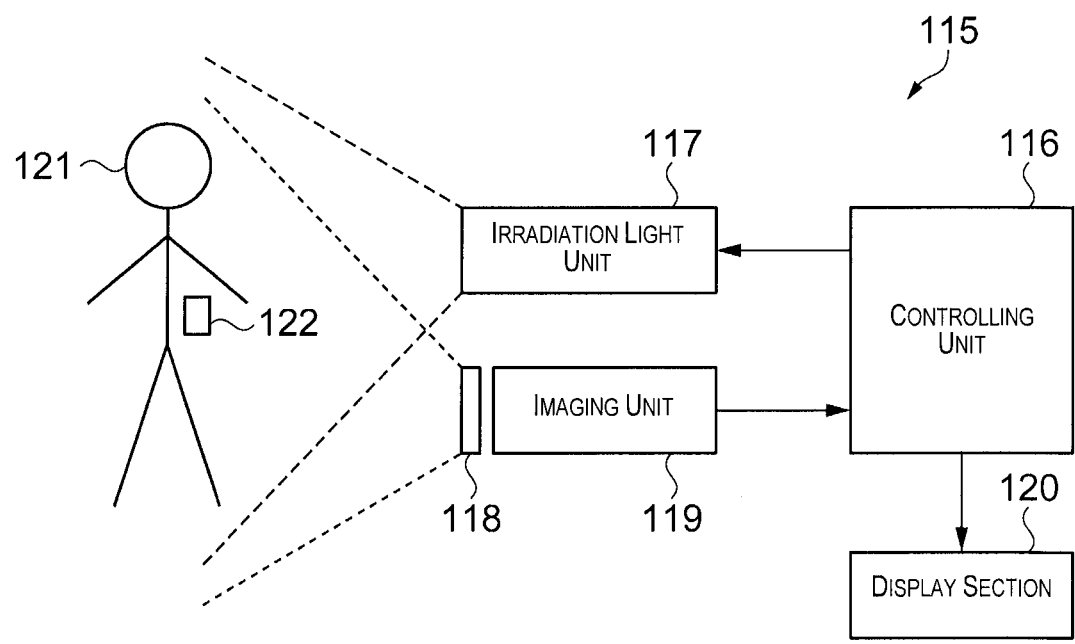
FIG. 14 is a block diagram showing a configuration of a specific substance detecting device according to an eighth embodiment.

Next, an embodiment of a specific substance detecting device that is one of the electronic devices provided with the infrared detecting element in its infrared detecting section will be explained with reference to FIG. 14. FIG. 14 is a block diagram showing a configuration of the specific substance detecting device.

As shown in FIG. 14, the specific substance detecting device 115 as the electronic device has a controlling unit 116, an irradiation light unit 117, an optical filter 118, an imaging unit 119, and a display section 120. The imaging unit 119 has an optical system such as a lens that is not shown in the drawing, and a light detecting section. The light detecting section is configured to have the infrared detecting element 1 in which the absorbing wavelength of the light absorbing member used in the infrared detecting section 3 of the infrared detecting element 1 according to the first embodiment is adjusted to be in a terahertz range. Alternatively, the light detecting section is configured to have the infrared detecting element 45 in which the absorbing wavelength of the light absorbing member used in the infrared detecting section 3 of the infrared detecting element 45 according to the second embodiment is adjusted to be in a terahertz range.

The controlling unit 116 includes a system controller that controls the entire specific substance detecting device 115, and the system controller controls a light source driving section and an image processing unit that are included in the controlling unit. The irradiation light unit 117 includes a laser device and an optical system for emitting terahertz light that is electromagnetic waves having a wavelength within a range of 100 μm to 1000 μm, and an object person 121 to be measured is irradiated by the terahertz light. The terahertz light reflected on the person 121 is received by the imaging unit 119 through the optical filter 118 that transmits only an optical spectrum of a specific substance 122 to be detected. The image processing unit of the controlling unit 116 conducts predetermined image processing to image signals generated in the imaging unit 119, and the image signals are output to the display section 120. The presence of the specific substance 122 can be judged because the intensity of the received signal is different based on whether the specific substance 122 is present or not in the clothes and the like of the person 121.

As described above, the present embodiment has the following effect:

(1) According to the present embodiment, the specific substance detecting device 115 has the light detecting section in the imaging unit 119, and the infrared detecting element 1 or the infrared detecting element 45 is used in the light detecting section. Since the infrared detecting element 1 or the infrared detecting element 45 used in the light detecting section 57 can detect infrared rays with good sensitivity, the specific substance detecting device 115 can serve as an electronic device provided with the infrared detecting element that can detect infrared rays with good sensitivity in the imaging unit 119.

Several embodiments are explained as above, but a person skilled in the art can easily understand that various modifications can be possible without substantially departing from the subject matter or the effect of the invention. Accordingly, these modifications are included in the scope of the invention. For example, a term described together with a different term having a broader or the same meaning in the specification or the drawings at least once can be replaced with the different term in any part of the specification or the drawings.

The invention can be widely applied to various pyroelectric detectors. The wavelength of detected light is not limited. Electronic devices having a pyroelectric detector or a pyroelectric detecting device, or those can be applied to a flow sensor and the like that detects a flow rate of a fluid under the conditions that a supplied heat amount and a heat amount the fluid deprives of are in equilibrium, for example. Instead of a thermocouple and the like provided in this flow sensor, the pyroelectric detector or the pyroelectric detecting device of the invention can be provided, and an object to be detected can be other than light.

The embodiment of the invention is not limited to the above-described embodiments, and various modifications and improvements can be possible. Modification examples will be described hereinafter.

MODIFICATION EXAMPLE 1

Figure 15:
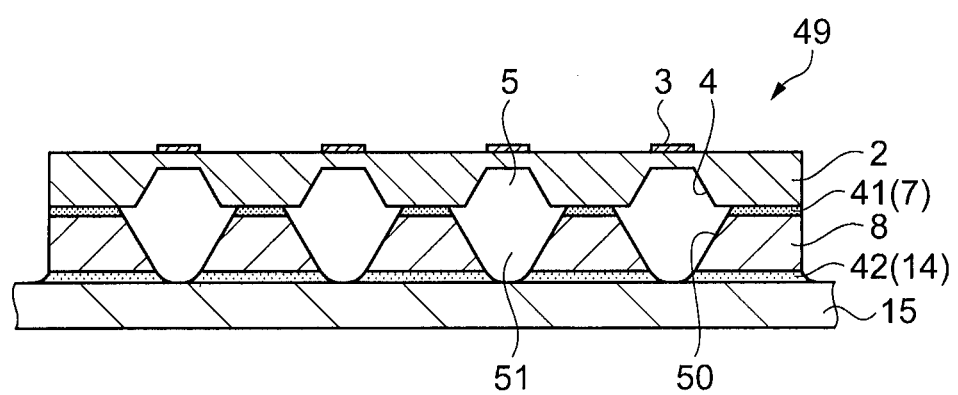
FIG. 15 is a sectional side diagram showing the main part of a configuration of an infrared detecting element according to a modification example.

In the first embodiment, the depth of the second recessed portion 9 formed in the second base plate 8 is smaller than the thickness of the second base plate 8. FIG. 15 is a sectional side diagram showing the main part of a configuration of the infrared detecting element according to this modification example. As shown in an infrared detecting element 49 of FIG. 15, a second recessed portion 50 formed in an area of the second base plate 8 that faces the first recessed portion 4 can penetrate through the second base plate 8. Further, the volume of a second hollow space portion 51 surrounded by the second recessed portion 50 can be greater than the volume of the adhesive 41 and the adhesive 42 that flow into the second recessed portion 50. In this case, the adhesive 41 and the adhesive 42 do not flow into the first hollow space portion 5, and thus the adhesive 41 and the adhesive 42 do not easily adhere to the first recessed portion 4.

MODIFICATION EXAMPLE 2

In the first embodiment, the first recessed portion 4 does not penetrate through the first base plate 2, but the first recessed portion 4 can penetrate through the first base plate 2. The infrared detecting section 3 can be supported by a beam. In this instance, heat will not easily be released by transmitting from the infrared detecting section 3 to the first base plate 2, and thus the sensitivity of the infrared detecting section 3 can be improved.

MODIFICATION EXAMPLE 3

In the first embodiment, the side wall 9a is inclined with respect to the second back surface 8b. However, the side wall 9a can be orthogonal with respect to the second back surface 8b if the surface tension of the adhesive 41 is great with respect to the side wall 9a. The adhesive 41 can easily move to the bottom portion 9c by causing the gravity to act on the adhesive 41.

MODIFICATION EXAMPLE 4

In the infrared detecting element 1 of the first embodiment, the infrared detecting sections 3 are arranged in four rows and four columns. However, the number of the infrared detecting sections 3 is not limited to a particular one, and the number of the infrared detecting sections 3 can be 1-15, or 17 or more. In this case, the adhesive 41 can be prevented from adhering to the first recessed portion 4 by providing the second base plate 8 in which the second recessed portion 9 is formed.

MODIFICATION EXAMPLE 5

In the first embodiment, the channel portions between recessed portions 12 are formed between all the neighboring second recessed portions 9. However, the channel portions between recessed portions 12 can not be formed between all the neighboring second recessed portions 9. One channel portion between recessed portions 12 or one outside connecting channel portion 13 can be provided with respect to one second recessed portion 9. The amount of etching the second base plate 8 can be reduced, and the second base plate 8 can be manufactured with good productivity.

MODIFICATION EXAMPLE 6

In the first embodiment, the infrared detecting element 1 has the integrated circuit 35. However, if the number of the infrared detecting sections 3 is small, the integrated circuit 35 does not need to be provided. The first wiring 24 and the second wiring 25 connecting to the infrared detecting sections 3 can directly be connected to the wiring 39 of the mounting substrate 15 by the bonding wire 40. Since there is no integrated circuit 35, the infrared detecting element can be manufactured with good productivity.

What is claimed is:

1. An infrared detecting element comprising:
   a first base plate that has a first surface, a second surface on the opposite side of the first surface, a first recessed portion provided in the second surface, and an infrared detecting section for detecting infrared rays provided in an area of the first surface that opposes the first recessed portion;
   a second base plate that has a third surface, a fourth surface on the opposite side of the third surface, and a second recessed portion provided in an area of the fourth surface that faces the first recessed portion; and
   an adhesion film that bonds the second surface and the fourth surface,
   wherein a second outer peripheral portion where the second recessed portion intersects with the fourth surface surrounds a first outer peripheral portion where the first recessed portion intersects with the second surface, and
   the second base plate has a side surface, and the second base plate has a channel portion formed in the second base plate between the second recessed portion and the side surface.

2. The infrared detecting element according to claim 1, wherein a side wall of the second recessed portion is inclined with respect to the fourth surface.

3. The infrared detecting element according to claim 1, wherein an additional first recessed portion and an additional infrared detecting section are provided in the first base plate, and the first recessed portion and the additional first recessed portion are provided in an area that faces the second recessed portion.

4. The infrared detecting element according to claim 1, wherein the second base plate has a plurality of the second recessed portions, and the second base plate has channel portions between the second recessed portions.

5. The infrared detecting element according to claim 1, wherein a bottom portion of the second recessed portion shields a hollow space portion surrounded by the first recessed portion and the second recessed portion from the third surface.

6. An electronic device having a light detecting section that detects infrared rays,
   wherein the light detecting section has the infrared detecting element according to claim 1.

7. The infrared detecting element according to claim 1, wherein a plurality of the infrared detecting sections are provided in the first base plate in a matrix pattern of a plurality of rows and a plurality of columns.

* * * * *